United States Patent
Isely et al.

(10) Patent No.: US 9,150,826 B2
(45) Date of Patent: Oct. 6, 2015

(54) PORTABLE SAMPLE DISRUPTOR APPARATUS, KITS, AND METHODS

(75) Inventors: Nikolas M. Isely, Moraga, CA (US); Marc E. Van Eden, North Tustin, CA (US); Jonathan K. Brown, Lake Forest, CA (US)

(73) Assignee: Zymo Research Corporation, Irvine, CA (US)

( * ) Notice: Subject to any disclaimer, the term of this patent is extended or adjusted under 35 U.S.C. 154(b) by 208 days.

(21) Appl. No.: 13/419,178

(22) Filed: Mar. 13, 2012

(65) Prior Publication Data

US 2012/0237925 A1  Sep. 20, 2012

Related U.S. Application Data

(60) Provisional application No. 61/452,464, filed on Mar. 14, 2011.

(51) Int. Cl.
| | |
|---|---|
| *C12M 1/02* | (2006.01) |
| *C12N 1/06* | (2006.01) |
| *C12Q 1/68* | (2006.01) |
| *C12M 1/00* | (2006.01) |
| *G01N 1/28* | (2006.01) |
| *G01N 33/48* | (2006.01) |
| *B01F 15/02* | (2006.01) |
| *C12N 15/10* | (2006.01) |
| *B01F 5/06* | (2006.01) |

(52) U.S. Cl.
CPC .............. *C12N 1/066* (2013.01); *C12M 47/06* (2013.01); *G01N 1/286* (2013.01); *B01F 5/0685* (2013.01); *B01F 15/0279* (2013.01); *B01F 2015/0273* (2013.01); *B01L 2400/0433* (2013.01); *C12M 1/02* (2013.01); *C12N 15/10* (2013.01); *C12N 15/1003* (2013.01)

(58) Field of Classification Search
USPC ..................................... 435/6.1, 306.1, 308.1
See application file for complete search history.

(56) References Cited

U.S. PATENT DOCUMENTS

| | | | |
|---|---|---|---|
| 4,675,298 A * | 6/1987 | Brusewitz .................. 435/305.1 |
| D668,563 S | 10/2012 | Isely et al. |
| 2001/0043883 A1 * | 11/2001 | Chalk .............................. 422/81 |
| 2005/0054958 A1 * | 3/2005 | Hoffmann ....................... 601/46 |
| 2005/0064395 A1 * | 3/2005 | Israel et al. ........................ 435/5 |
| 2005/0084957 A1 * | 4/2005 | Atwood et al. ............ 435/304.1 |
| 2006/0110725 A1 * | 5/2006 | Lee et al. ........................... 435/5 |
| 2007/0071647 A1 * | 3/2007 | Kim et al. ...................... 422/68.1 |
| 2008/0131949 A1 * | 6/2008 | Bortolin et al. ............. 435/173.9 |
| 2010/0031757 A1 * | 2/2010 | Hoyer ......................... 73/863.01 |
| 2010/0159507 A1 | 6/2010 | Ting et al. |
| 2011/0014673 A1 * | 1/2011 | Hukari et al. ................ 435/173.1 |
| 2011/0250680 A1 * | 10/2011 | Broyer et al. .................. 435/325 |
| 2012/0003654 A2 * | 1/2012 | Belgrader et al. ............ 435/6.12 |

OTHER PUBLICATIONS

"12 Sample Tissue Homogenizer with cooling fan", Apr. 5, 2010, retrieved from http://www.wisbiomed.com, retrieved on Aug. 22, 2011.

(Continued)

*Primary Examiner* — Jennifer Wecker
(74) *Attorney, Agent, or Firm* — Parker Highlander PLLC (57) ABSTRACT

Apparatuses, kits, and methods for portable sample disruption (e.g., for encouraging cell lysis).

21 Claims, 8 Drawing Sheets

(56) References Cited

OTHER PUBLICATIONS

"Advantages of Sample Extraction Using the PCT Shredder," Nov. 2, 2009, retrieved from http://www.pressurebiosciences.com/pub/Shredder-Data.pdf, retrieved on Aug. 22, 2011.

"Complete disruption of *Caenorhabditis elegans* under non-denaturing conditions using pressure cycling technology (PCT)", BioTechniques Protocol Guide, 2009, p. 53, retrieved from www.BioTechniques.com/protocol.

"Craftsman 11818 Nextec 12-volt Lithium-Ion Cordless Hammerhead Auto Hammer ENERGY STAR®", Feb. 16, 2009, retrieved from http://www.sears.com, retrieved on Aug. 23, 2011.

"News Release: Pressure BioSciences, Inc. and Omni International Announce Marketing, Distribution, and Technology Development Agreement", Dec. 11, 2008, retrieved from http://www.pressurebiosciences.com/news_releases/article-242.html on Aug. 22, 2011.

"Next Advance Field Blender Enhancement" Jan. 2, 2011, retrieved from http://nextadvance.com, retrieved on Aug. 22, 2011.

"The PCT Shredder Kit", Product Specification Sheet, Pressure Biosciences, Inc., 2009.

"Tissue Homogenizer Field Portable Enhancement Pack", Jan. 11, 2011, retrieved from http://www.wisbiomed.com on Aug. 22, 2011.

Hou et al., "Diabetes reduces aortic endothelial gap junctions in ApoE-deficient mice: simvastatin exacerbates the reduction", *Journal of Histochemistry and Cytochemistry*, 56(8):745-752, 2008.

Schewe and Aguirre-Ghiso, "ATF6alpha-Rheb-m TOR signaling promotes survival of dormant tumor cells in vivo", Proc Natl Acad Sci USA., 105(30): 10519-24, 2008. (Supporting Information).

* cited by examiner

PORTABLE SAMPLE DISRUPTOR APPARATUS, KITS, AND METHODS

CROSS-REFERENCE TO RELATED APPLICATIONS

This application claims priority to U.S. Provisional Patent Application No. 61/452,464, filed Mar. 14, 2011, which is incorporated by reference here in its entirety.

BACKGROUND

1. Field of the Invention

The present invention relates generally to sample disruption (e.g., for cell lysis). More particularly, but not by way of limitation, the present invention relates to portable or in-field sample disruption.

2. Background Information

Degradation and contamination of biological samples have been obstacles to scientific study, and may be particularly problematic in highly sensitive molecular-analysis techniques. For example, reliability of techniques such as single molecule sequencing and quantitative polymerase chain reaction (PCR) generally depends upon high-quality, unadulterated, biological samples. In a laboratory setting sterile equipment and careful technique can prevent contamination of samples. Likewise, cryogenic freezing and/or limiting exposure to high temperature may be utilized to attempt to maintain the integrity of samples. For collection of biological samples in the field, such as in forensics and environmental science, use of cryogenic freezing is generally too impractical to be employed.

SUMMARY

The present disclosure includes embodiments of apparatuses, kits, and methods.

Embodiments of the present apparatuses comprise: a body defining a chamber having a first end and a second end configured to permit a container (e.g., vial) to be inserted into the chamber, the body configured to be coupled to a device having a piston such that the volume of the chamber can be varied by reciprocating the piston between a retracted position and an extended position; and a cap configured to be coupled to the body such that the cap covers the second end of the chamber; where if the body is coupled to the device, the piston can be reciprocated to vibrate a container (e.g., vial) disposed in the chamber.

Some embodiments of the present apparatuses further comprise: a resilient member coupled to at least one of the cap and the body such that if a container (e.g., vial) is vibrated in the chamber, the resilient member is compressed when the piston is in the extended position. In some embodiments, the body comprises threads, and the cap comprises threads corresponding to the threads of the body for coupling the cap to the body. In some embodiments, the cap comprises a retractable protrusion biased in a bias direction that is toward at least a portion of the body when the cap is coupled to the body; the body comprises a plurality of indents; and the apparatus is configured such that if coupled to the body the cap is rotatable to adjust the length of the chamber between innermost and outermost positions of the cap at which the retractable protrusion of the cap will extend into one of the plurality of indents of the body to resist rotation of the cap relative to the body. In some embodiments, the cap includes a shoulder configured such that if a container (e.g., vial) is disposed in the chamber and the cap is coupled to the body, the shoulder will limit lateral movement of the container (e.g., vial). In some embodiments, the cap includes one or more openings configured to permit fluid communication through the cap if the cap is coupled to the body.

In some embodiments, the body is configured to fit within a rectangular volume of 12 cubic inches. In some embodiments, the body and cap are configured to be coupled together such that the body and cap fit within a rectangular volume of 16 cubic inches. Some embodiments of the present apparatuses further comprise a device having a piston; where the body is coupled to the such that the volume of the chamber can be varied by reciprocating the piston between a retracted position and an extended position. In some embodiments, the device is battery powered. In some embodiments, the device is an auto-hammer.

Some embodiments of the present kits comprise; an embodiment of the present apparatuses, and a battery charger. Some embodiments further comprise: one or more containers (e.g., vials) each sized to be vibrated in the chamber of the body. Some embodiments further comprise: at least one component selected from the group consisting of: earplugs, lysis beads, lysis solutions, an instruction manual, and a battery.

Some embodiments of the present methods comprise: providing an embodiment of the present apparatuses (e.g., comprising a body and a cap, the body defining a chamber having a first end and a second end, and the cap configured to be coupled to the body such that the cap covers the second end of the chamber); and coupling the body to a device having a piston (e.g., such that: the volume of the chamber can be varied by reciprocating the piston between a retracted position and an extended position; and/or the piston can be reciprocated to vibrate a container (e.g., vial) disposed in the chamber).

Some embodiments of the present methods comprise: providing an embodiment of the present apparatuses (comprising a body and a cap, the body defining a chamber having a first end and a second end, and the cap configured to be coupled to the body such that the cap covers the second end of the chamber, where the body is coupled to a device having a piston such that the volume of the chamber can be varied by reciprocating the piston between a retracted position and an extended position); disposing a container (e.g., vial) in the chamber; coupling the cap to the body; and activating the device to vibrate the container (e.g., vial). In some embodiments, the device is held such that the cap is above at least a portion of the device while the device is activated. In some embodiments, the container (e.g., vial) includes a body portion and a lid portion, and the container (e.g., vial) is disposed in the chamber such that at least part of the lid portion of the container (e.g., vial) is disposed between the cap and the body portion of the container (e.g., vial). In some embodiments, the device is activated for at least 30 seconds. Some embodiments further comprise: disposing a sample in the vial prior to disposing the vial in the chamber.

Some embodiments of the present methods comprise: mechanically disrupting a cell sample disposed in a container such that nucleic acid is released from cells in the sample; where mechanically disrupting includes activating a battery-powered device of an apparatus (e.g., one of the present apparatuses) to cause reciprocation of a piston to vibrate the container.

In some embodiments of the present methods, the container contains a sample (e.g., a cell sample). In some embodiments, the container contains a plurality of beads. In some embodiments, the beads comprise ceramic. In some embodiments, the container contains a lysis solution. In some embodiments, the lysis solution comprises an organic lysis solution. In some embodiments, the sample (e.g., cell sample) comprises soil, fecal matter, or biological tissue. In some embodiments, the container comprises a storage tube.

In any embodiment of the present disclosure, the term "substantially" may be substituted with "within [a percentage] of" what is specified, where the percentage includes 5, 10, and/or 15 percent.

Any embodiment of any of the present systems and/or methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

Details associated with the embodiments described above and others are presented below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers.

DESCRIPTION OF ILLUSTRATIVE EMBODIMENTS

The term "coupled" is defined as connected, although not necessarily directly, and not necessarily mechanically; two items that are "coupled" may be integral with each other. The terms "a" and "an" are defined as one or more unless this disclosure explicitly requires otherwise. The terms "substantially," "approximately," and "about" are defined as largely but not necessarily wholly what is specified, as understood by a person of ordinary skill in the art.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method that "comprises," "has," "includes" or "contains" one or more steps possesses those one or more steps, but is not limited to possessing only those one or more steps. Likewise, a watering system that "comprises," "has," "includes" or "contains" one or more elements possesses those one or more elements, but is not limited to possessing only those elements. For example, in a watering system that comprises one or more surfaces and a platform, the watering system includes the specified elements but is not limited to having only those elements. For example, such a watering system could also include a drainage structure.

Further, a device or structure that is configured in a certain way is configured in at least that way, but it can also be configured in other ways than those specifically described.

At least some embodiments of the present apparatuses, kits, and methods relate to portable apparatuses (e.g., battery-powered and/or compact apparatuses) for disrupting cell samples (e.g., for cell lysis). Samples obtained in the field may be difficult to transport to a lab for analysis in such a way that degradation of the sample is prevented or reduced. At least some embodiments of the present apparatuses, kits, and methods permit (i) rapid processing of a sample into a stabilizing buffer that can prevent or reduce sample degradation; (ii) rapid processing in a way that avoids or reduces the likelihood of contamination (which is generally difficult to achieve outside of the laboratory setting); and/or (iii) rapid processing with an apparatus that is easily transportable and efficient to operate in the field.

Referring now to the drawings, and more particularly to FIGS. 1-10, shown therein and designated by the reference numeral 10 is one embodiment of the present portable sample-disruption apparatuses. In the embodiment shown, apparatus 10 comprises a body 14, and a cap 18 configured to be coupled to body 14. Body 14 and/or cap 18 may comprise any suitable material, such as, for example, one or more polymers (e.g., polyamide (also known as NYLON), polyoxymethylene (POM) (also known as acetal or DELRIN), acrylonitrile butadiene styrene (ABS), polyvinyl chloride (PVC)), and/or one or more metals (e.g., aluminum, stainless steel, titanium, alloys, and the like). Body 14 and cap 18 may comprise the same material(s) and/or may comprise different materials. For example, in one embodiment, body 14 comprises polyoxymethylene or acetal, and cap 18 comprises ABS.

Figure 1:
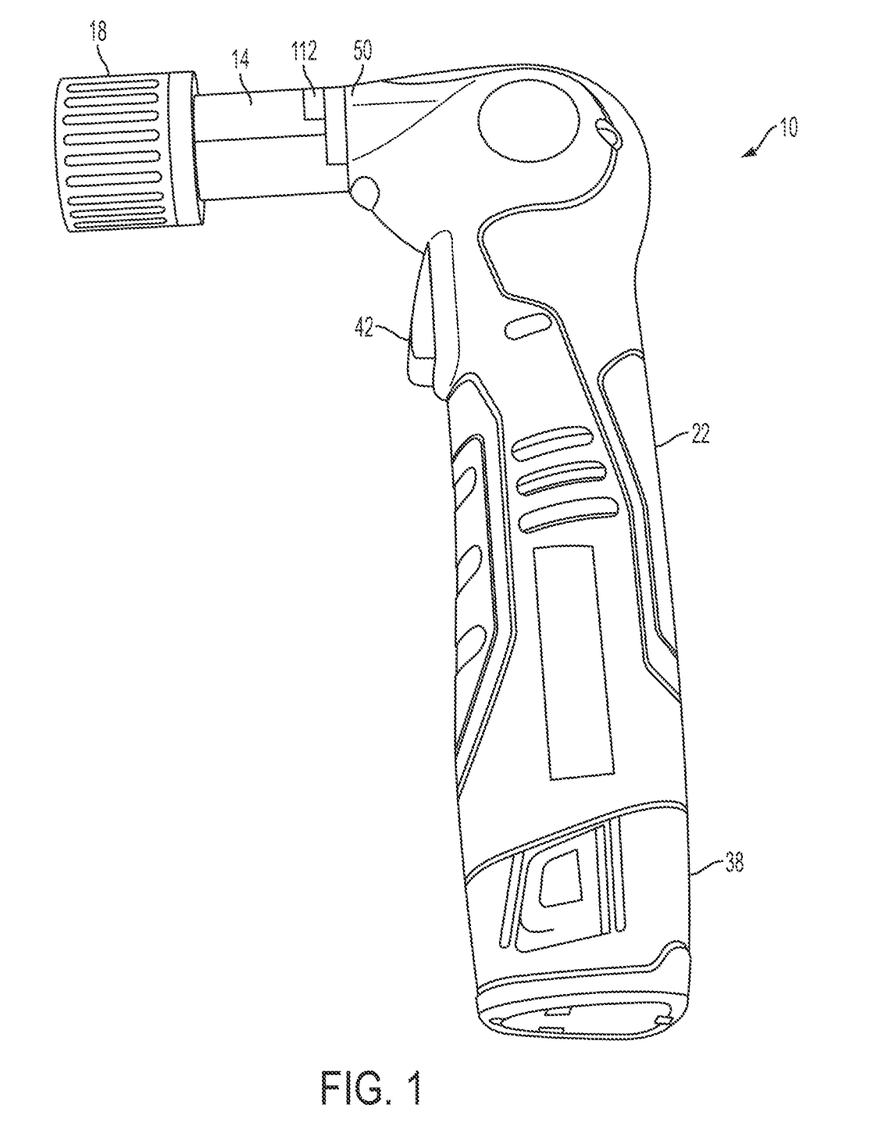
FIG. 1 depicts is a perspective view of one of the present portable sample-disruption apparatuses coupled to an auto-hammer.
Figure 6:
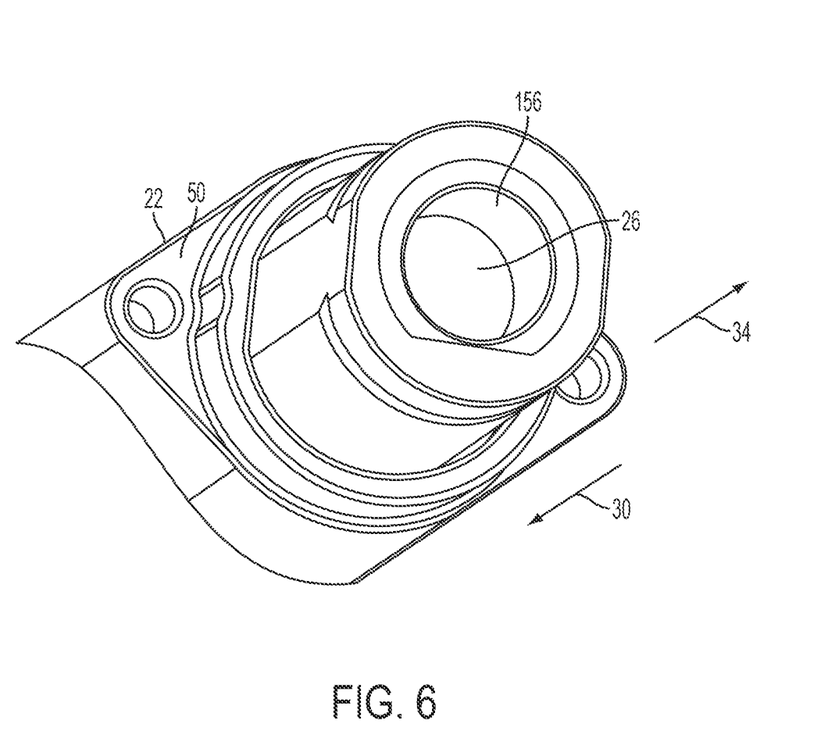
FIG. 6 depicts an enlarged perspective view of a portion of the auto-hammer of FIG. 1.
Figure 7A:
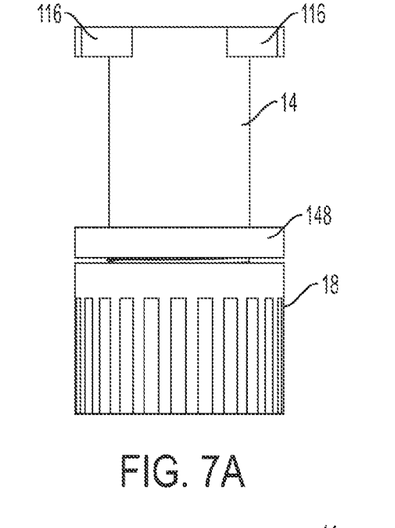
FIGS. 7A-7D depict various enlarged views of the apparatus of FIG. 1.
Figure 7B:
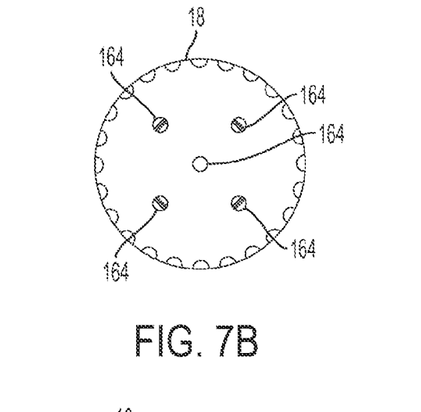
Figure 7C:
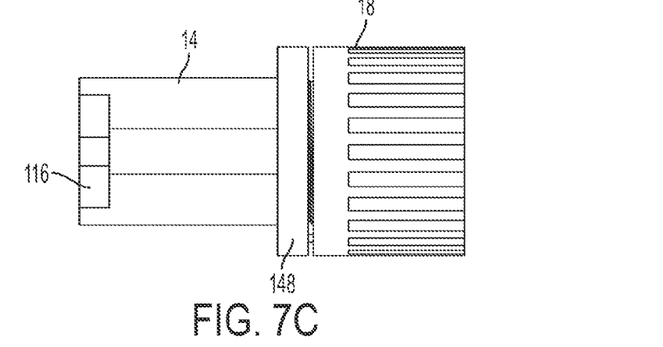
Figure 7D:
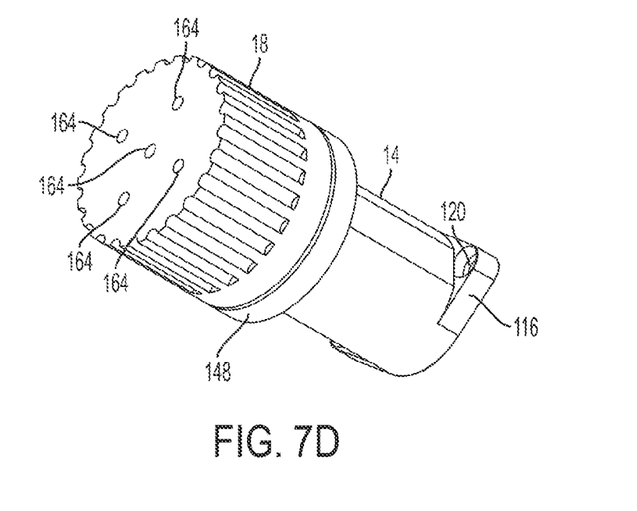

As also shown, body 14 is configured to be coupled to device 22 having a piston 26 configured to reciprocate between a retracted position (innermost position in direction 30) and an extended position (outermost position in direction 34). Device 22 may, for example, be an auto-hammer (e.g., such as is available from Sears Brands LLC under the CRAFTSMAN brand, U.S.A. under the name "Craftsman 11818 Nextec 12-volt Lithium-Ion Cordless Hammerhead Auto Hammer"). In the embodiment shown, device 22 is battery powered, and comprises a removable battery (e.g., battery pack) 38. In other embodiments, battery pack 38 may not be removable. In the embodiment shown, device 22 also includes a trigger 42 configured to be depressed to activate device 22 and thereby reciprocate piston 26. In the embodiment shown, device 22 is configured such that activation of device 22 will not translate to reciprocation of piston 26 unless some force is applied to piston 22 in direction 30 (e.g., to engage the piston with the internal drive mechanism (not shown) of device 22 to cause the piston to be drive in direction 34 and/or direction 30). In other embodiments, piston 26 may reciprocate whenever device 22 is activated (e.g., regardless of whether pressure is applied to piston 26 in direction 30). As used in this disclosure, "reciprocate" includes alternating motion of piston 26 in directions 30 and 34, and does not require that the piston is driven in both directions (e.g., the piston may be driven in direction 34 and simply recoil in direction 30), nor that the piston travels at the same speed in both of directions 30 and 34 (e.g., in a sinusoidal fashion).

In the embodiment shown, apparatus 10 is configured as a portable, hand-held device, that can be used for vigorous cell disruption outside of a laboratory setting (e.g., in remote locations and in various weather conditions). For example, apparatus 10 can be used as described in more detail below to disrupt cells in and/or from samples (e.g., of yeast, bacteria, plant, soil, fecal, animal tissue, and the like). Likewise, in the embodiment shown, apparatus 10 is configured for use in nearly any location (e.g., if battery 38 is sufficiently charged), and in various weather conditions, for rapid processing of sample collections (e.g., to preserve and improve stability of processed samples). In the embodiment shown, apparatus 10 is configured to receive a container 46 (e.g., a 2-milliliter (mL) vial or "tube") within body 14 for disruption of a sample disposed in the container, as described in more detail below. Containers such as 2-mL vials are known, and are available with "skirted" or pointed bottoms. In some embodiments of the present apparatuses and methods, vials with skirted bottoms are used or included. In some embodiments, the container comprises a storage tube. In the embodiment shown, trigger 42 can be depressed for any desired length of time for disruption of a sample, permitting customization and individual control over the duration of sample disruption. In some embodiments, device 22 includes a timer (e.g., a timer circuit) configured to enable activation of device 22 for pre-set durations (e.g., 30, 45, 60, 90, 120, and/or 180 seconds).

Figure 2:
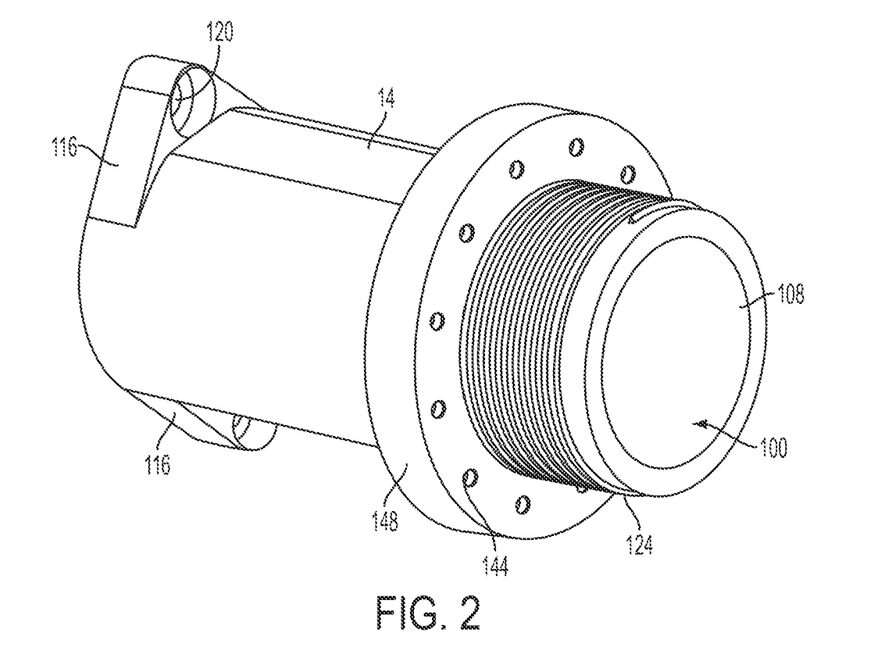
FIG. 2 depicts a perspective view of a body of the apparatus of FIG. 1.
Figure 5:
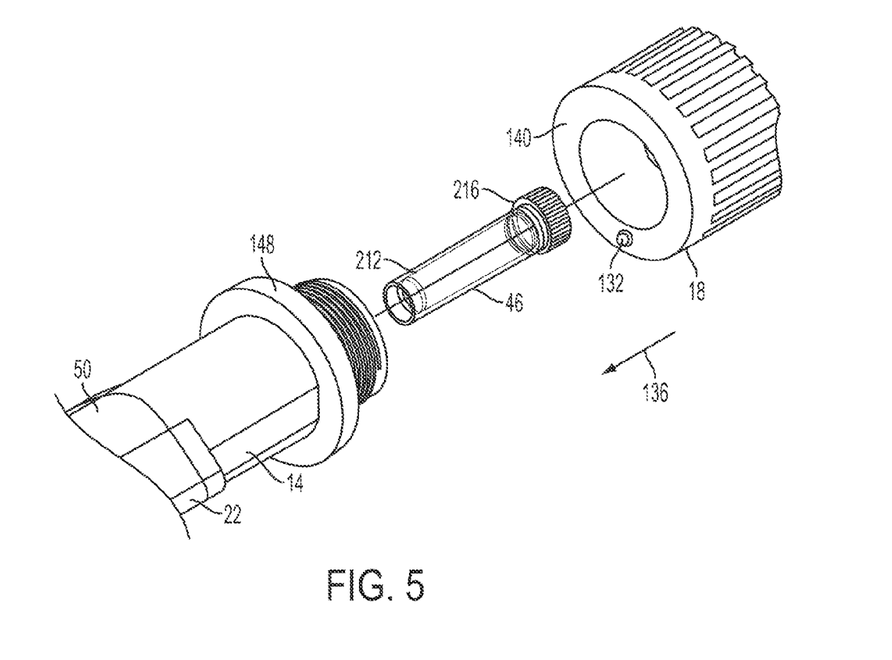
FIG. 5 depicts a perspective exploded view of the apparatus of FIG. 1.

In the embodiment shown, body 14 defines a chamber 100 having a first end 104 and a second end 108. In the embodiment shown, second end 108 of chamber 100 is configured to permit a vial 46 to be inserted into chamber 100. Body 14 is configured to be coupled to (and is shown coupled to) device 22. For example, in the embodiment shown, device 22 includes a coupling portion 50 to which body 14 is configured to correspond and be coupled (e.g., via screws 112). In the embodiment shown, body 14 includes flange portions 116 extending from opposite lateral sides of the body, and including holes 120 positioned to align with matching holes in attachment portion 50 of device 22. Other embodiments may include only a single flange portion (e.g., extending around the entire perimeter of the body). In the embodiment shown, screws 112 comprise machine screws with 10-32 threads having a length of approximately 0.75 inches, such as, for example, machine screws configured to be driven by an Allen or star wrench or bit. Other embodiments may include any suitable fasteners that couple body 14 to device 22 such that apparatus 10 can function as described in this disclosure. In the embodiment shown, cap 18 is configured to be coupled to body 14 such that cap 18 covers second end 108 of chamber 100. Apparatus 10 is configured such that, if body 14 is coupled to device 22, as shown, piston 26 can be reciprocated (e.g., by depressing trigger 42) to vibrate a vial 46 that is disposed in chamber 100 (e.g., with cap 18 coupled to body 14 to cover second end 108 and retain the vial in the chamber).

Figure 3:
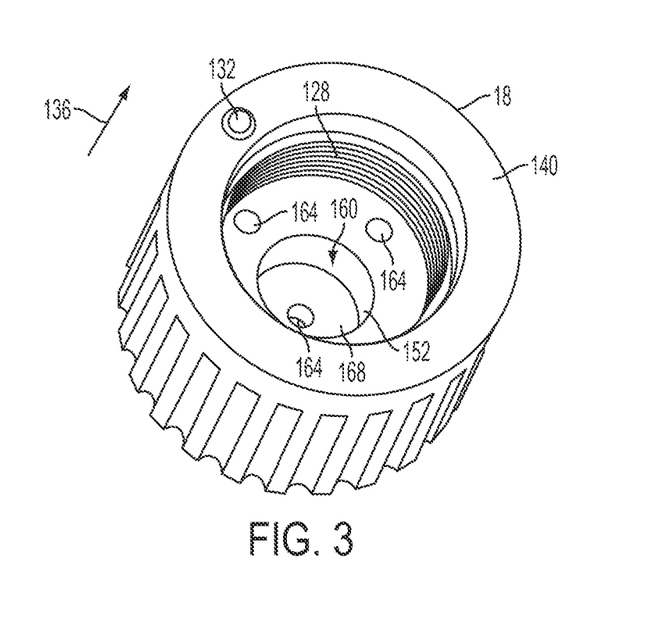
FIG. 3 depicts a perspective view of the cap of the apparatus of FIG. 1.
Figure 4:
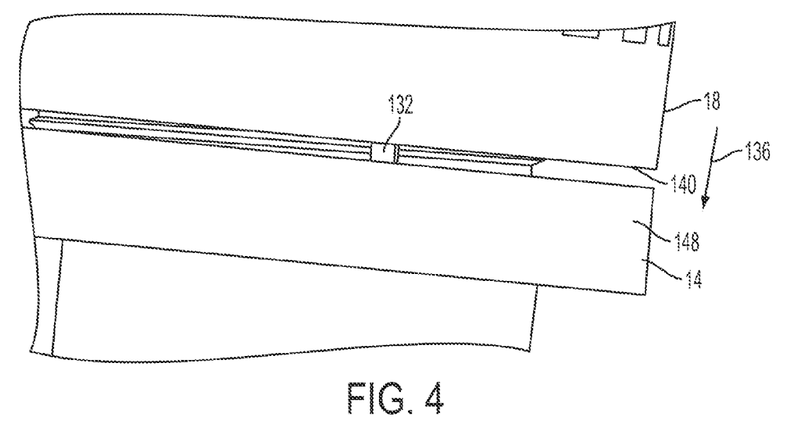
FIG. 4 depicts an enlarged perspective view of the cap of FIG. 3 coupled to the body of FIG. 2.

In the embodiment shown, body 14 comprises threads 124, and cap 18 comprises threads 128 corresponding to threads 124 for coupling the cap to the body. In the embodiment shown, cap 18 is configured such that if coupled to body 14, cap 18 is rotatable to adjust the distance between piston 26 and cap 18 (e.g., to accommodate vials of different lengths). In the embodiment shown, cap comprises a retractable protrusion 132 biased in a bias direction 136 (that is toward at least a portion of body and/or first end 104 of cavity 100) when the cap is coupled to the body. Retractable protrusion 132 need not be entirely retractable (e.g., may not be capable of retracting below bottom surface 140 of cap 18) and/or may be entirely retractable (e.g., may be capable of retracting below bottom surface 140). In the embodiment shown, bias direction 136 is substantially parallel to the central longitudinal axis of cavity 100. In other embodiments, bias direction may be non-parallel to the central longitudinal axis of cavity 100. In the embodiment shown, retractable protrusion 132 comprises a ball catch in which a ball is biased in bias direction 136 by a spring (not shown), such that the ball catch extends beyond surface 140 in the absence of a force compressing the biasing spring.

In the embodiment shown, body 14 comprises a plurality of indents 144. More particularly, in the embodiment shown, body 14 includes a flange 148 around at least a portion of a perimeter of the body, and indents 144 are disposed on flange 148 at equiangular intervals around the body. In this embodiment, apparatus 10 is configured such that if coupled to body 14, cap 18 is rotatable to adjust the length of the chamber between innermost and outermost positions of the cap at which retractable protrusion 132 will extend into one of indents 144 to resist rotation of the cap relative to the body. For example, the outermost position of the cap is the position of the cap at which the portion of protrusion 132 extending into one of the indents 144 is sufficient to resist rotation of the cap relative to the body, and the innermost position of the cap is the position at which the cap is prevented (e.g., by surface 140 and flange 148, protrusion 132 and flange 148, and/or by a vial 46 in cavity 100) from being rotated or any closer to the body (e.g., flange 148).

In the embodiment shown, cap 18 includes a shoulder 152 (in the interior of the cap) configured such that if a vial 46 is disposed in chamber 100 and cap 18 is coupled to body 14, shoulder 152 will limit lateral movement of the vial (e.g., will maintain sufficient alignment between the vial and piston 26). Similarly, in the embodiment shown, device 3 includes a shoulder 156 (that extends around and beyond piston 26) configured such that if a vial 46 is disposed in chamber 100 and cap 18 is coupled to body 14, shoulder 152 will limit lateral movement of the vial (e.g., will maintain sufficient alignment between the vial and piston 26). In other embodiments, shoulder 156 may be included in body 100 (e.g., may be defined by body 14), such as, for example, between first end 104 and second end 108 of cavity 100 (e.g., at or near first end 104). As shown, shoulder 152 defines a central portion 160 within the perimeter of shoulder 152. The distance between central portion 160 and bottom surface 140 is greater than the distance between shoulder 152 and bottom surface 140, such that in use, a vial 46 extends within the perimeter of shoulder 152.

In the embodiment shown, cap 18 also includes one or more openings 164 configured to permit fluid communication through the cap if the cap is coupled to the body. For example, as noted above, reciprocation of piston 26 varies the volume of chamber 100 such that when the piston is extended, the pressure in chamber 100 could increase beyond an acceptable level. Openings 164 are configured to permit pressure in the chamber to equalize to pressure outside the chamber. In the embodiment shown, cap 18 includes a central opening 164 in central portion 160 (within the perimeter of shoulder 152), and four peripheral openings outside the perimeter of shoulder 152. Other embodiments may include openings 164 in any suitable number or configuration.

In the embodiment shown, apparatus 10 further comprises a resilient member 168 coupled to at least one of cap 18 and body 14 such that if a vial 46 is vibrated in chamber 100 (with cap 18 coupled to body 14), resilient member 168 is compressed when piston 26 is in the extended position. For example, in the embodiment shown, resilient member 168 comprises a resilient washer (e.g., comprising rubber, polyurethane, or any other suitably resilient material) disposed in central portion 160. In some embodiments, resilient member 168 is a rubber washer having an outer diameter of ½ inch, an inner diameter of 3/16 inch, and an uncompressed (relaxed) thickness of 1/16 inch.

As noted above, in the embodiment shown, apparatus 10 is configured to be portable and compact. For example, in the embodiment shown, body 14 is configured to fit within a rectangular volume of 12 cubic inches (e.g., a rectangular box with dimensions of 2 inches by 2 inches by 3 inches), or smaller (e.g., 10 cubic inches, 8 cubic inches, or less). By way of another example, in the embodiment shown, body 14 and cap 18 are configured to be coupled together such that body 14 and cap 18 fit within a rectangular volume of 16 cubic inches, or smaller (e.g., 12 cubic inches, 10 cubic inches, or less).

Some embodiments of the present methods comprise: coupling one of the present apparatuses (e.g., 10, comprising body 14 and cap 18, the body defining a chamber having a first end and a second end, and the cap configured to be coupled to the body such that the cap covers the second end of the chamber) to a device (e.g., 22) having a piston (e.g., 26), such that the volume of the chamber (e.g., 100) can be varied by reciprocating the piston between a retracted position and an extended position; and the piston can be reciprocated to vibrate a vial disposed in the chamber. For example, in one embodiment, a device 22 is modified by creating or enlarging holes in connection portion 50 (to correspond to holes 120 and screws 112). Holes that are created or enlarged in device 22 may be pre-threaded, or may be threaded by insertion of screws 112 (e.g., if screws 112 are self-tapping).

Some embodiments of the present methods comprise: mechanically disrupting a cell sample disposed in a container (e.g., 46) such that nucleic acid is released from cells in the sample; where mechanically disrupting includes activating a battery-powered device (e.g., 22) of an apparatus (e.g., 10) to cause reciprocation of a piston (e.g., 26) to vibrate the container.

Some embodiments of the present methods comprise: providing an embodiment of the present apparatuses (e.g., 10, with body 14 coupled to a device such as, for example, device 22); disposing a vial (e.g., 46) in the chamber of the apparatus; coupling the cap (e.g., 18) to the body (e.g., 14); and activating the device (e.g., 22) to vibrate the vial. In some embodiments, the device (and/or the apparatus) is held such that the cap (e.g., 18) is above at least a portion of the device while the device is activated. For example, the device can be held such that the body and cap are oriented vertically with the cap above the body (and such that the vial in the chamber is also oriented vertically). As illustrated, vials 46 each can include a body portion 212 and a lid portion 216. In some embodiments of the present methods, the vial is disposed in chamber 100 such that at least part of lid portion 216 of the vial is disposed between the cap and the body portion of the vial (e.g., such that lid portion 216 is adjacent cap 18, and/or within shoulder 152 in central portion 160 of the cap).

In some embodiments of the present methods, the vial can contain: a sample (e.g. a soil sample), a plurality of beads (e.g., lysis beads), and/or a lysis solution (e.g., an organic lysis solution). In some embodiments of the present methods, the device is activated for at least 30 seconds (e.g., any of the durations mentioned above). Some embodiments of the present methods comprise disposing a sample in the vial prior to disposing the vial in the chamber. For example, samples (e.g., cell samples) can comprise soil, fecal matter, or biological tissue (fungal/bacterial, tissue & insect, plant/seed, and the like). Various test kits for DNA and RNA testing and sample preparation from Zymo Research Corporation.

Figure 8:
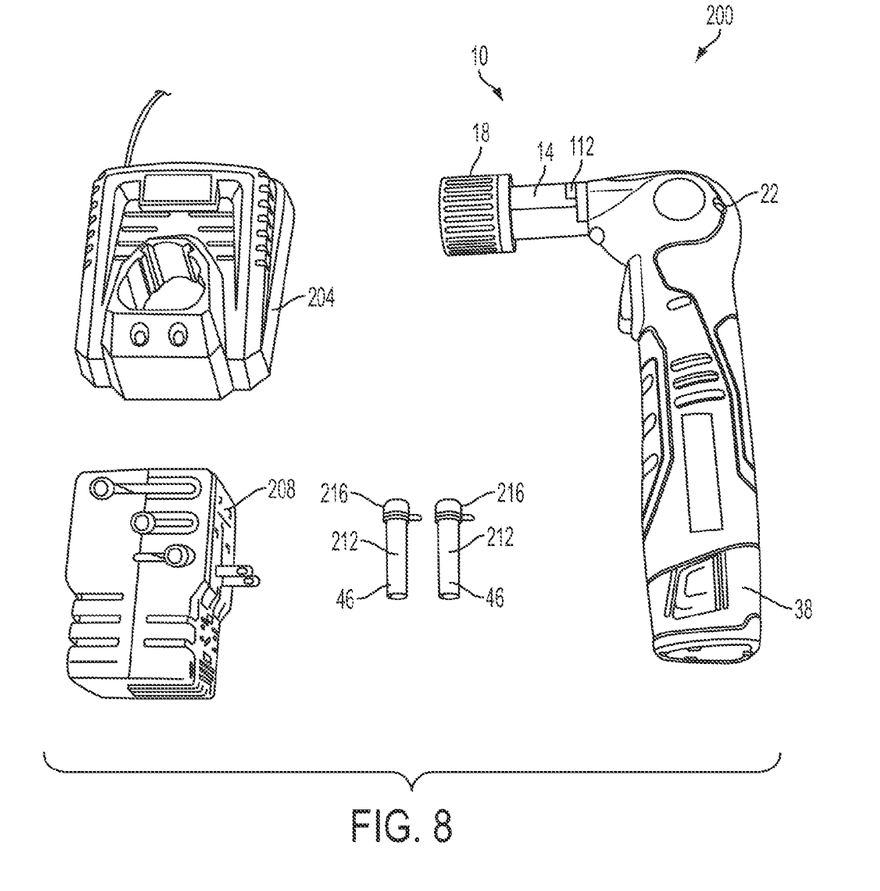
FIG. 8 depicts a perspective view of one of the present kits.
Figure 9:
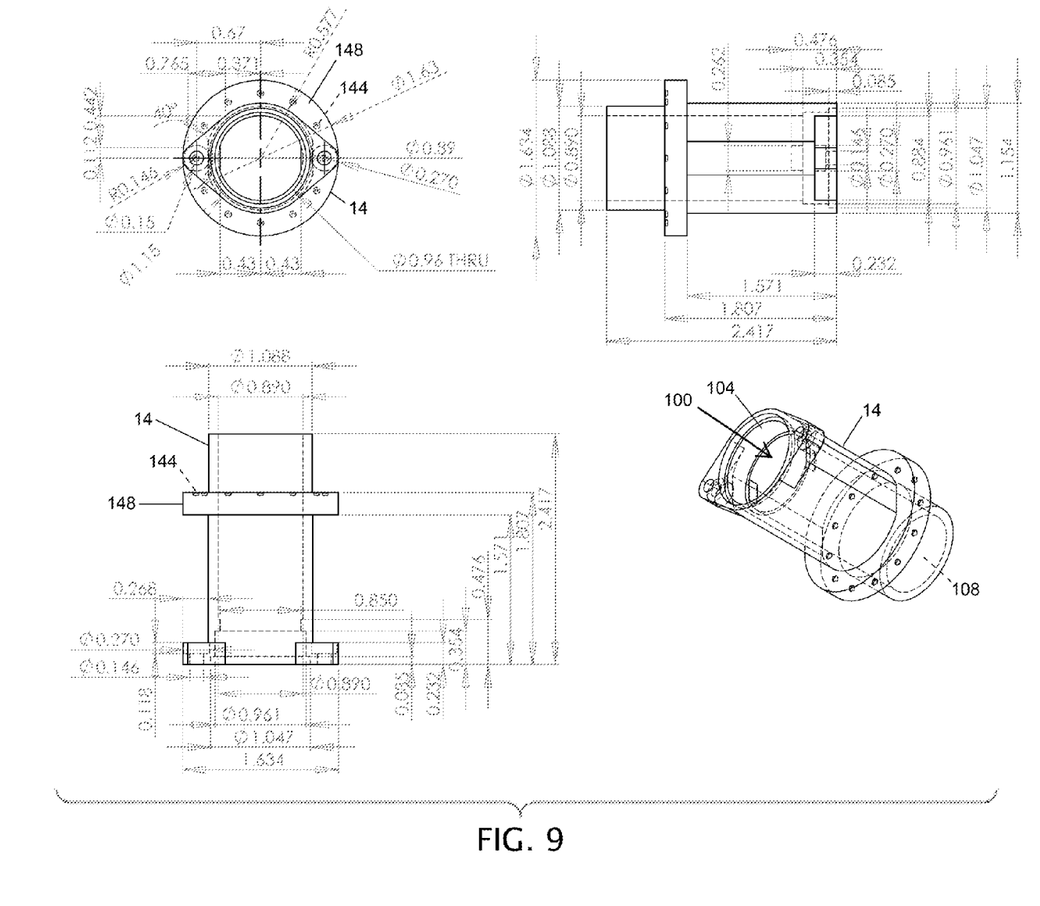
FIG. 9 depicts various dimensioned views of one embodiment of the body of FIG. 2.
Figure 10:
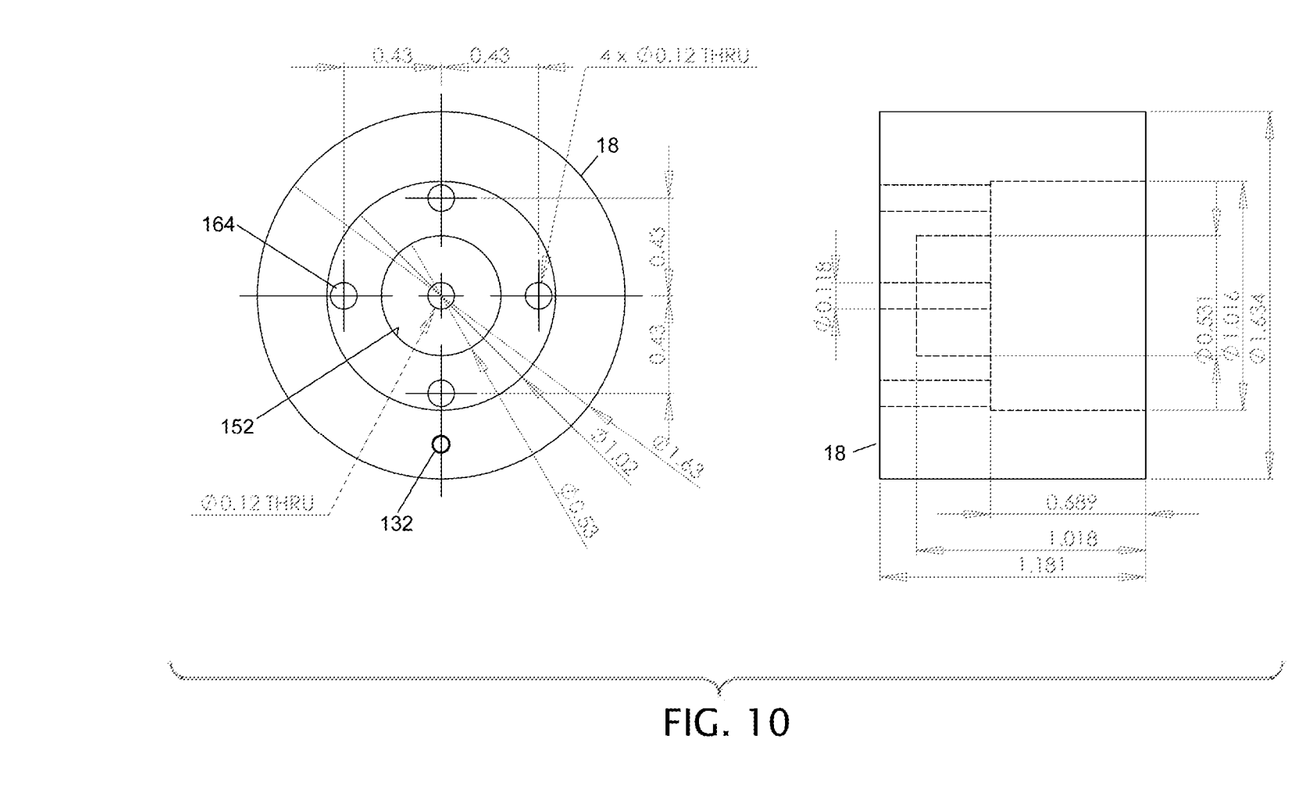
FIG. 10 depicts various dimensioned views of one embodiment of the cap of FIG. 3.

FIG. 10 depicts on embodiment of the present kits 200. In the embodiment shown, kit 200 comprises an apparatus 10 with device 2, and a battery charger 204 configured to charge battery 38. In some embodiments, the present kits may also comprise one or more (e.g., two) vials 46, each sized to be vibrated in chamber 100 of body 14. In some embodiments, kit 200 further comprises at least one component selected from the group consisting of: earplugs (not shown), lysis beads and/or lysis solutions (e.g., lysis solutions and/or ceramic lysis beads, such as, for example, those available from Zymo Research Corporation, California, U.S.A.), an instruction manual, and a battery 38 (e.g., an extra or second battery). In some embodiments, kit 200 can also include a converters 208 configured to convert available power (e.g., AC power) in various locations (e.g., international locations with varying standards for power delivery). In some embodiments, vials 46 may contain lysis beads (not shown), such as, for example, a plurality of 2 millimeter beads and/or a plurality of 0.5 millimeter beads (e.g., 5 2 mm beads and 5-0.5 mm beads).

The various illustrative embodiments of devices, systems, and methods described herein are not intended to be limited to the particular forms disclosed. Rather, they include all modifications and alternatives falling within the scope of the claims. For example, the caps of the present apparatuses can be configured to be coupled to the bodies of the present apparatuses by any suitable structure (e.g., interlocking tabs and grooves).

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. An apparatus comprising:
    a body defining a chamber having a first end and a second end configured to permit a container to be inserted into the chamber;
    one or more containers positioned within said chamber, said one or more containers for containing a biological sample comprising cells; and
    a cell lysing device coupled to the body, wherein said cell lysing device consists essentially of a battery operated mechanical reciprocating vibrator configured to vibrate said one or more containers to lyse said cells in the biological sample, said one or more containers optionally including one or more lysis beads and/or a lysis solution.

2. The apparatus of claim 1, where the apparatus further comprises a battery charger configured to charge a battery for the device.

3. A method comprising:
    disrupting a cell sample disposed in a container such that nucleic acid is released from cells in the sample,
    said disrupting consisting essentially of providing reciprocated vibration to the cell sample by activating a battery-powered mechanical disrupting device of an apparatus, optionally, wherein the container includes one or more lysis beads and/or a lysis solution.

4. The method of claim 3, where the container contains one or more lysis beads.

5. The method of claim 3, where the container contains a lysis solution.

6. The method of claim 3, where the cell sample comprises soil, fecal matter, or biological tissue.

7. The method of claim 3, wherein the container comprises a storage tube.

8. The method of claim 3, where the apparatus comprises an apparatus of claim 1.

9. The method of claim 5, wherein the lysis solution is an organic lysis buffer.

10. The method of claim 3, further comprising contacting the cell sample with a stabilizing buffer to prevent or reduce sample degradation.

11. The method of claim 4, wherein the lysis beads comprise ceramic beads.

12. The method of claim 3, wherein the disrupting device comprises a removable battery pack.

13. The method of claim 3, wherein the container is a 2 ml tube.

14. The method of claim 3, wherein the apparatus is configured to be handheld.

15. The method of claim 3, wherein the disrupting device comprises a reciprocating piston.

16. The apparatus of claim 1, wherein the chamber of the body is configured to permit a 2 ml storage container.

17. The apparatus of claim 1, wherein the container comprises one or more lysis beads.

18. The apparatus of claim 1, wherein the container comprises a biological cell sample.

19. The apparatus of claim 1, wherein the device comprises a removable battery pack.

20. The apparatus of claim 1, wherein the reciprocating vibrator is a reciprocating piston.

21. The apparatus of claim 1, wherein the body is configured to fit within a rectangular volume of 12 cubic inches.

* * * * *

UNITED STATES PATENT AND TRADEMARK OFFICE
CERTIFICATE OF CORRECTION

PATENT NO. : 9,150,826 B2
APPLICATION NO. : 13/419178
DATED : October 6, 2015
INVENTOR(S) : Nikolas M. Isely et al.

It is certified that error appears in the above-identified patent and that said Letters Patent is hereby corrected as shown below:

In the Claims

In claim 1, column 8, line 52, after "solution" insert --, wherein the said apparatus is configured to be hand-held--.

Signed and Sealed this
Twenty-eighth Day of June, 2016

Michelle K. Lee
*Director of the United States Patent and Trademark Office*